United States Patent
Mancino

(10) Patent No.: US 9,579,487 B2
(45) Date of Patent: Feb. 28, 2017

(54) WATERPROOF CHEST CATHETER PROTECTOR SHEATH

(71) Applicant: Carl Michael Mancino, North Hollywood, CA (US)

(72) Inventor: Carl Michael Mancino, North Hollywood, CA (US)

(73) Assignee: Patricia Lee Ambrose, North Hollywood, CA (US)

( * ) Notice: Subject to any disclaimer, the term of this patent is extended or adjusted under 35 U.S.C. 154(b) by 0 days.

(21) Appl. No.: 14/263,157

(22) Filed: Apr. 28, 2014

(65) Prior Publication Data

US 2014/0323967 A1 Oct. 30, 2014

Related U.S. Application Data

(60) Provisional application No. 61/854,639, filed on Apr. 29, 2013.

(51) Int. Cl.
*A61M 25/01* (2006.01)
*A61M 1/36* (2006.01)

(52) U.S. Cl.
CPC ........ *A61M 25/0111* (2013.01); *A61M 1/3661* (2014.02); *A61M 2209/06* (2013.01)

(58) Field of Classification Search
CPC ............ A61M 25/0111; A61M 1/3661; A61M 2209/06; A61M 25/01; A61M 25/02; A61M 2025/0246; A61M 2025/0253; A61M 2025/0273; A61M 2025/028; A61M 25/0017

See application file for complete search history.

(56) References Cited

U.S. PATENT DOCUMENTS

| | | | | |
|---|---|---|---|---|
| 4,767,411 A * | 8/1988 | Edmunds | ...................... | 604/180 |
| 5,415,642 A * | 5/1995 | Shepherd | ...................... | 604/344 |
| 6,222,090 B1 * | 4/2001 | Weston | .......................... | 602/41 |
| 2008/0208145 A1 * | 8/2008 | McCulloch | .................... | 604/263 |

OTHER PUBLICATIONS http://www.cathdry.com/product/catheter/cath-dry , http://www.cathdry.com/about-us.*
https://web.archive.org/web/20121015014714/http://www.thechemicalblog.co.uk/potassium-permanganate-uses , Richard Huson , Potassium Permanganate Uses, Oct. 15 2012.*
"CoverCath," Screen capture of www.covercath.com on May 17, 2014, available at http://web.archive.org/web/20140517075846/http://covercath.com/.

(Continued)

*Primary Examiner* — Manuel Mendez

(57) ABSTRACT

A single piece, single cavity, reusable waterproof catheter cover having an elongated body closed at the bottom end with a catheter entry opening to the cavity (C) surrounded by a flange (A) at the opposite top end. When the wrapped or unwrapped catheter and the catheter's entry port into the body are encased in the catheter housing (B), the flange lies flat against the skin and a waterproof adhesive film patch having a hole (D) in the center is used to affix the flange to the skin all the way around, providing a secure water-tight seal. The cover is made out of a pliable yet sturdy, durable, easily sanitized, medical grade material that allows the cover to be reused frequently and indefinitely.

20 Claims, 3 Drawing Sheets

(56) References Cited

OTHER PUBLICATIONS

"Liqua Shield," http://liquashield.com/, retrieved on Dec. 23, 2015.
"Shower C.A.P.," Screen capture of http://www.sdaproduct.net on Dec. 22, 2014, available at http://web.archive.org/web/20141222234112/http://www.sdaproduct.net/.
"Shower Shield Water Barrier," http://www.showershield.net, retrieved on Dec. 23, 2015.
"KOR shield," http://www.korshield.com, retrieved on Dec. 23, 2015.

* cited by examiner

WATERPROOF CHEST CATHETER PROTECTOR SHEATH

CROSS-REFERENCE TO RELATED APPLICATIONS

This application claims the benefit of U.S. Provisional Application No. 61/854,639, filed Apr. 29, 2013 by the present inventor.

BACKGROUND

Performing the function that damaged kidneys cannot do effectively, hemodialysis is a process whereby a machine intercepts blood flow, removes toxins and excess water, and returns the cleansed blood to the body in an uninterrupted continuous circulation. This is accomplished with the aid of two methods of blood retrieval and return (i.e., through a tube [a hemodialysis catheter implanted in and protruding out of the chest] or a "fistula" [an artery-vein connection within the arm]). The preparation of a patient for hemodialysis is a two-step process involving the following surgical procedures:
1. the insertion of the catheter into the upper chest cavity—half of its length inside the body and half of its length hanging loosely outside of the chest cavity—for the purpose of immediately beginning dialysis, and
2. the creation of the fistula by connecting an artery to a vein buried under the skin inside one arm.

The fistula will ultimately become the permanent port for hemodialysis. However, it requires maturation time for the fistula to heal properly—anywhere from 3 to 6 months—in order to be usable. Therefore, the catheter is the initial means to begin hemodialysis up until the fistula under the skin is ready for use, at which time the catheter is removed.

The fistula under the skin is accessed by using two large hypodermic needles inserted at the beginning of each session and removed at the end of each session. The needle insertion points close over and heal between each treatment so there is no risk of infection from waterborne contaminants.

However, some people's skin and arm flesh react poorly to this method, and the catheter must be relied upon indefinitely.

Unlike the needle used with the fistula, the catheter remains permanently in place during its months or years of use, leaving a possible avenue for infection to enter the body. To minimize the risk of infection, the end of the catheter that protrudes from the body is lightly wrapped in fresh gauze by the nurse. Before each hemodialysis treatment, the wrap is taken off from around the catheter and at the end of the treatment a fresh gauze wrap is applied around the catheter. All this time, the catheter does not move from its implanted position. Since the gauze wrap is not waterproof, moisture and water coming in contact with any part of the catheter or its entry port into the body present a serious risk of infection. Consequently, the patient is cautioned to keep dry the catheter's components and entry port.

This restriction poses obvious problems with regard to bathing, showering, and swimming.

There are several types of waterproof hemodialysis catheter covers available to protect the catheter and its entry port from water infiltration, each with its own disadvantages.

Korshield is a reusable, soft plastic, rubber-collared one-piece cape that is pulled on and off over the head and used for showering only. The collar can come unglued or stretch, and there is some discomfort after showering because the cape is dripping wet and the material quickly gets cold. In addition, it is sold in three sizes so obtaining the correct size is essential in order for the product to be effective.

Cover Cath (for shower and bath only), Liquishield (for shower only), Shower C.A.P. (for shower only), and Shower Shield (for shower only) are one-time use, disposable products that employ a plastic bag configuration or plastic film sheet with an adhesive material around the underside perimeter that seals to the skin. Most appear to require considerable manipulation to apply and remove. Cath Dry (for shower, bath, and swimming) is also a one-time use, disposable product. In addition, the examples of these competing products, with the exception of Cover Cath, are shown using an unwrapped catheter. This suggests that the unskilled patient may be required to take extra, time-consuming steps to unwrap and re-wrap the catheter every time he/she wants to bathe.

DETAILED DESCRIPTION

In accordance with one embodiment a waterproof catheter protector sheath comprises a single piece, single cavity, injection molded tubular sheath, closed at one end with an opening surrounded by a flange at the top end.

Accordingly several advantages of one or more aspects are as follows: to provide a waterproof catheter protector sheath that is reusable, that is more economical over time, that encases a wrapped or unwrapped catheter, and that is simple to apply and remove. Other advantages of one or more aspects will be apparent from a consideration of the drawings and ensuing description.

Drawings—Reference Letters

Figure 1:
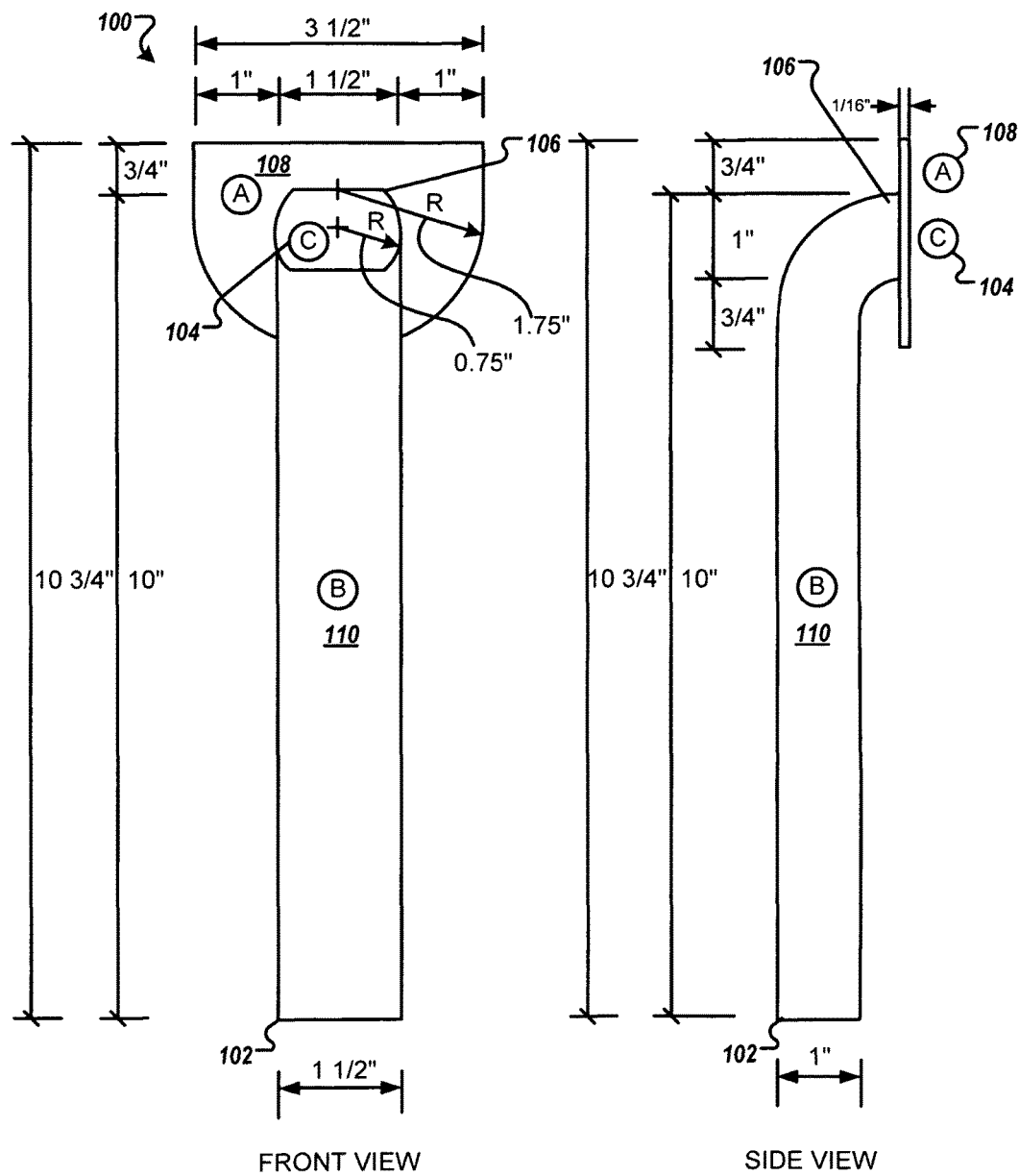
FIG. 1 shows various aspects of the protector sheath in accordance with the embodiment.

A flange
B catheter housing (portion of protector sheath in which the catheter is inserted and rests)
C catheter entry opening to protector sheath
D hole located in the center of the adhesive film patch FIG. 1 shows various aspects of a protector sheath 100 in accordance with the embodiment. The embodiment of my protector sheath is illustrated in FIG. 1. The single piece protector sheath 100 is closed at a bottom end 102 with a catheter entry opening C 104 to the protector sheath 100 at an opposite top end 106 that is surrounded by a flange A 108. A catheter housing B 110, the portion of the protector sheath in which the catheter rests, is tubular in shape but can be any other shape that lends itself to the purpose at hand. The embodiment of my protector sheath 100 is typically injection molded of a waterproof, light weight, pliable yet sturdy, durable, easily sanitized material such as medical grade silicone rubber or dynaflex, a plastic compound that exhibits rubber-like characteristics. However, the protector sheath 100 can be composed of any other material that possesses the desired properties and/or qualities. The material can be transparent, translucent, semi-translucent, opaque, or colored. With technological advances, the protector sheath 100 can be manufactured by any other method or technique, such as 3D printing.

The protector sheath 100 is approximately 10.75 inches long by 1.5 inches wide by 0.125 inches thick. The flange A 108 is approximately 2.5 inches high by 3.5 inches wide. In one embodiment, the material of the protector sheath 100 is medical grade silicon with a wall thickness of ⅛ inch. The material may be solid white or translucent. In another embodiment, the material of the protector sheath 100 is medical grade dynaflex with a wall thickness of 1/16 inch.

In the depicted embodiment, the protector sheath 100 includes the elongated tubular body 110 of material that has a closed bottom end 102 and an open top end 106. The elongated tubular body 110 has closed sides from the closed bottom end 102 along a length of the elongated tubular body 110 up to an opening 104 at the open top end 106 to form a single cavity designed to encase a wrapped or unwrapped catheter (not illustrated in FIG. 1). In the depicted embodiment, the length of the elongated tubular body 110 is greater in dimension than a width of the elongated tubular body 110. For example, the length may be 10 inches and the width is 1.5 inches. The protector sheath 100 also includes the flange 108 disposed at the open top end 106 to surround the opening 104. The elongated tubular body 110 and the flange 108 are a single piece of the material. In the depicted embodiment, the flange includes: a first surface that extends out from the opening 104 in a first plane, the first surface to be disposed on a first portion of skin; and a second surface that extends out from a perimeter of the elongated tubular body 110 in a second plane parallel to the first plane, the second surface to affix to a first portion of an adhesive film product while a second portion of the adhesive film product affixes to a second portion of the skin that surrounds the first portion of the skin to seal the flange against the skin. In the depicted embodiment, a width of the flange is at least double a width of the opening. For example, the width of the flange is 3.5 inches and the opening is 1.5 inches.

Figure 2:
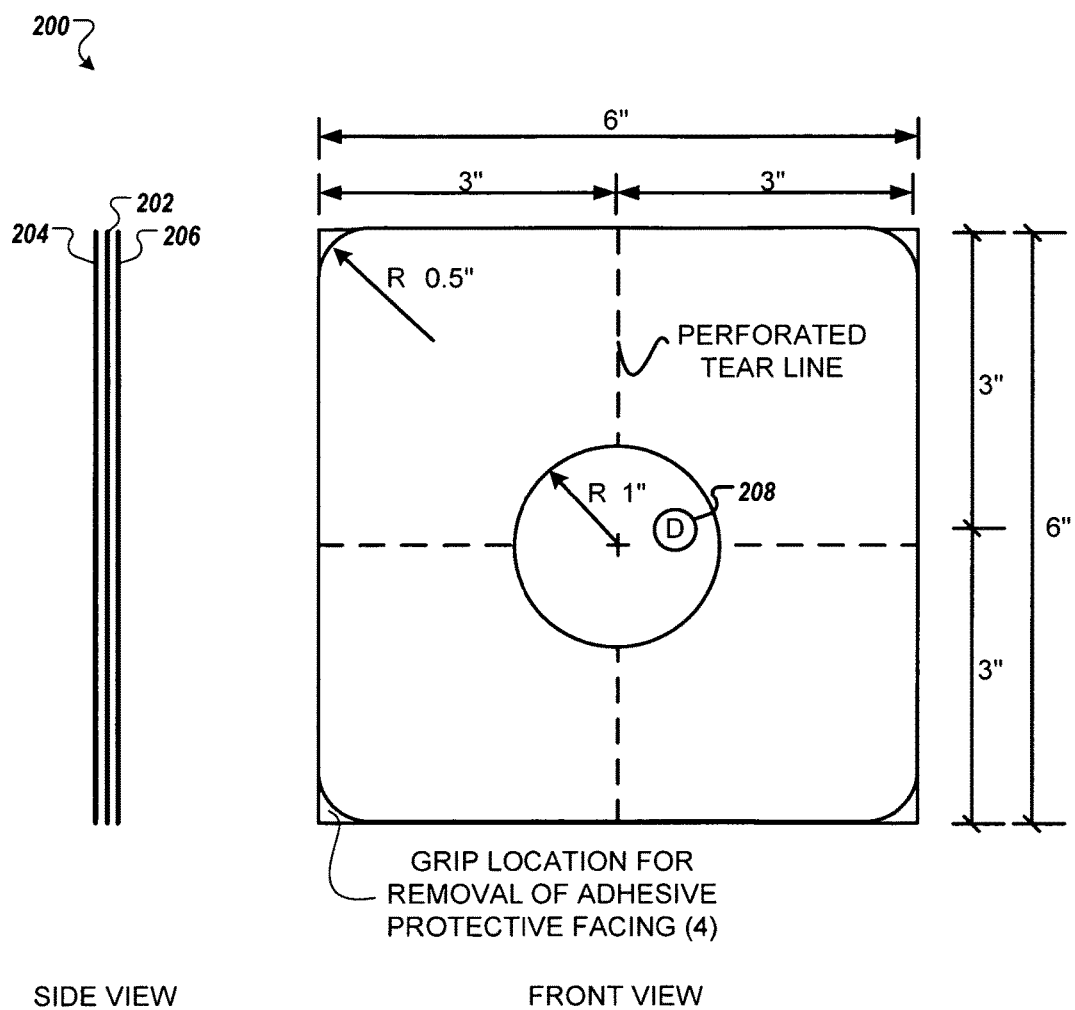
FIG. 2 shows various aspects of a waterproof FDA approved adhesive film patch product configured to my specifications in accordance with the embodiment.

Operation—FIGS. 1, 2

The manner of using the protector sheath 100 in order to safely shower, bathe, or swim is as follows:

The embodiment of my protector sheath 100 employs a flexible waterproof, single use, disposable adhesive film patch 200, illustrated in FIG. 2, to seal the flange A 108 to the skin. The patch 200 is approximately 6 inches long by 6 inches wide and comprises an adhesive side, a non-adhesive side, backing paper on both sides, and a custom die-cut hole D 208 located in the center as illustrated in the front view of FIG. 2. The custom die-cut hole D 208 is a central opening to fit around the shaft 110 of the protector sheath 100. As illustrated in the side view of FIG. 2, the patch with adhesive surface 202 is sandwiched between an adhesive protective facing 204 and a patch stiffener 206 to prevent curling. The patch stiffener 206 can be removed at time of patch application. Also, as illustrated in FIG. 2, there are four grip locations for removal of the adhesive protective facing 204. The patch 200 can include perforated tear lines as denoted by the dashed lines.

With the adhesive side 202 of the patch 200 facing upward and the backing papers 204, 206 in place, the patient or attendant drops the bottom of the protector sheath 100 through the hole D in the center of the adhesive patch 200. The adhesive patch 200 is slid up the catheter housing B 110 almost to the base of the flange A 108, at which point the backing paper 206 on the adhesive side of the patch 200 is peeled off. The exposed adhesive side 202 of the patch 200 is pressed against the front of the flange A 108, adhering to the flange A 108 with the exposed adhesive perimeter extending beyond the flange perimeter by approximately 1 inch. With the protruding catheter positioned at the catheter entry opening C 104 to the protector sheath 100, the entire protector sheath assembly is slid up the catheter until the flange A 108 lies flat against the chest, and the extended exposed adhesive perimeter is then pressed against the skin. The backing paper 206 is then removed from the non-adhesive side of the patch 200 (which is now facing outward), and the patch 200 is pressed more firmly against the skin on all sides, making sure that any creases or bubbles are flattened out, creating a water-tight seal against the chest and completely encasing the catheter and its entry port in a waterproof compartment.

The protector sheath 100 is removed by holding the catheter housing B 110 stationary with one hand while pulling the adhesive film 204 sideways from a corner with the other hand.

The protector sheath 100 can also be used to protect a peritoneal dialysis catheter, which protrudes from the abdomen, using the application/removal process described above.

The protector sheath 100 is sanitized by spraying it with alcohol. It can also be soaked in boiling water or microwaved. A battery operated ultraviolet wand that can be used to sanitize the unit is an option in the future. A moisture detection agent such as a form of litmus paper, a small permanganate crystal, etc. can be dropped into the protector sheath 100 prior to application. These items change color upon contact with moisture.

Figure 3:
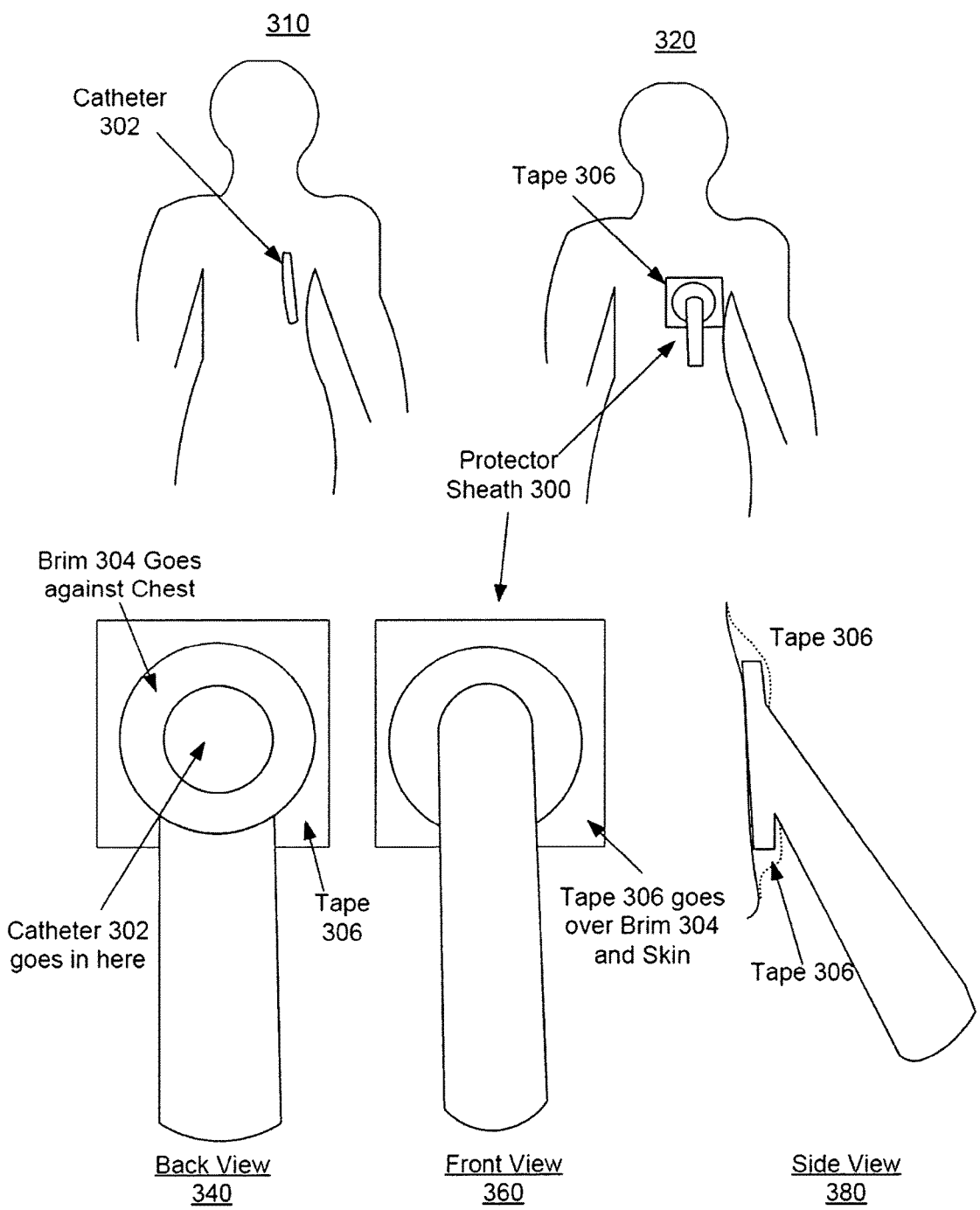
FIG. 3 shows a series of views of a protector sheath disposed over a catheter located on a chest of a patient according to one embodiment.

FIG. 3 shows a series of views of a protector sheath 100 disposed over a catheter located on a chest of a patient according to one embodiment. FIG. 3 shows a type of waterproof chest catheter protector sheath 300. Kidney dialysis patients begin treatment with a catheter 302 implanted in an upper chest area that hangs from the insertion site, at a downward angle, anywhere between five to six inches below the insertion site, as illustrated at view 310. The catheter 302 is often left in place for a minimum of three months and sometimes permanently. The catheter 302 should not be moved too much and cannot get wet, making normal showering or bathing impossible. View 320 illustrates a waterproof, hollow, tubular, single piece, molded silicone sheath 300. The sheath 300 is closed at the bottom. Around the top open end of the sheath is a thin flat "brim" 304, much like the brim of a hat, which rests against the skin creating a seal using waterproof adhesive tape 306. The open, brimmed end of the sheath 300, illustrated in the back view 340, is molded at an angle of approximately 20 to 30 degrees (illustrated in side view 380) since the catheter 302 protrudes from the chest at a downward angle. Starting at the bottom of the exposed end of the catheter 302, the sheath 300 is pulled up to enclose the catheter 302 (illustrated in front view 360 and side view 380), and the brim 304 is positioned flat against the chest and secured using waterproof adhesive tape 306, as illustrated in view 320. The dimensions of the sheath 300 are calculated to prevent movement of the catheter 302 during a shower or a bath. The sheath 300 can be reused for an indefinite period of time or until the catheter 302 is no longer required. The sheath 300 can be submerged in alcohol to sterilize it between uses.

In the depicted embodiment, a waterproof catheter sheath 300 includes an elongated tubular body comprising an opening at a proximal end through which a catheter 302 implanted in an upper chest area that hangs from an insertion site at a downward angle is inserted. The elongated tubular body is closed at a distal end. The elongated tubular body has closed sides from the distal end that is closed along a length of the elongated tubular body up to the opening at the proximal end to form a single cavity designed to encase the catheter, the length being greater in dimension than a width of the elongated tubular body. The waterproof catheter sheath 300 also includes a flange 304 integrated with the elongated tubular body at the proximal end to surround the opening. The flange 304 has a flat surface to rest against a first portion of skin of the upper chest around a perimeter of the insertion site. An adhesive film (e.g., tape 306) is disposed over a rear surface of the flange 304 to create a seal against a second portion of the skin that surrounds the first portion of the skin. The seal is created at a perimeter of the flange 304 that is located at a specified distance away from the insertion site, the specified distance being greater than a width of the opening of the elongated tubular body (e.g., see dimensions of FIG. 1). The elongated tubular body is molded at an angle to accommodate the catheter 302 that hangs from the insertion site at the downward angle.

Advantages

From the description above, a number of advantages of the embodiment of my protector sheath 100 become evident: (a) The protector sheath 100 is made out of a waterproof, pliable yet sturdy, durable, easily sanitized, medical grade material which allows it to be reused frequently and indefinitely. (b) The protector sheath 100 is more economical over time than disposable products. (c) The protector sheath 100 allows a more simplified positioning of the unit and application of the adhesive mechanism. (d) The protector sheath 100 can be used with a wrapped or an unwrapped catheter. (e) There is no adhesive on the underside of the flange A 108 itself that might come in contact with the catheter entry port and any sutures so there is no danger of pulling on the site. The configuration of the flange A 108 is such that the patch adhesive 202 is kept well away from the catheter entry port and any sutures allowing the protector sheath 100 to be used prior to suture removal. (f) With respect to traveling, it is far more convenient to carry a single protector sheath 100 and a supply of compact patches 200 in one's luggage than it is to pack a half dozen bulky disposable items of the same size in order to shower or bathe during a two week trip.

Conclusion, Ramifications, and Scope

Accordingly, the reader will see that the embodiment of my protector sheath 100 can be reused repeatedly and indefinitely. Furthermore, the protector sheath 100 has the additional advantages in that: it is more economical over time than disposable products; it allows a more simplified positioning of the unit and application of the adhesive mechanism; it can be used with a wrapped or an unwrapped catheter; the patch adhesive 202 is kept well away from the catheter entry port and any sutures meaning there is no danger of pulling on the site and allowing the protector sheath 100 to be used prior to suture removal; it is more convenient when traveling to carry a single protector sheath 100 and a supply of compact patches 200 in one's luggage than it is to pack a half dozen bulky disposable items in order to shower or bathe during a two week trip.

Although the description above contains many specificities, these should not be construed as limiting the scope of the embodiment but as merely providing illustrations of aspects of the embodiment. For example, the protector sheath 100 can vary in shape, size, and length depending on catheter dimensions; the flange A 108 and adhesive film patch 200 can vary in shape and size, etc.

Thus the scope of the embodiment should be determined by the appended claims and their legal equivalents, rather than by the examples given.

I claim:

1. A catheter cover comprising:
an elongated tubular body of material having a closed bottom end and an open top end, wherein the elongated tubular body has closed sides from the closed bottom end along a length of the elongated tubular body up to an opening at the open top end to form a single cavity designed to encase a catheter, the length being greater in dimension than a width of the elongated tubular body; and
a flange disposed at the open top end to surround the opening, wherein the elongated tubular body and the flange are a single piece of the material, wherein the flange comprises:
a first surface that extends out from the opening in a first plane, the first surface to be disposed on a first portion of skin; and
a second surface that extends out from a tubular perimeter of the elongated tubular body in a second plane parallel to the first plane, the second surface to affix to a first portion of an adhesive film product while a second portion of the adhesive film product affixes to a second portion of the skin that surrounds the first portion of the skin to seal the flange against the skin, wherein a relative width of the flange is at least double, the relative width being between a first width between opposing sides of an outer perimeter of the flange in the first plane and a second width between opposing sides of an inner perimeter of the flange in the first plane, the inner perimeter being defined by the opening, wherein the relative width being at least double increases a distance from the outer perimeter to the inner perimeter and increases an area of the second surface of the flange such that a force required to break a seal between the flange and the skin is increased.

2. The catheter cover of claim 1, wherein the catheter, wrapped or unwrapped, is encased in the elongated tubular body through the opening and the flange is secured to skin using the adhesive film product affixed to and extending beyond a front of the outer perimeter of the flange, sealing the flange to the skin, wherein the adhesive film product is a waterproof adhesive film product.

3. The catheter cover of claim 2 wherein the waterproof adhesive film product is a disposable adhesive patch having a hole in a center.

4. The catheter cover of claim 1 wherein the elongated tubular body comprises a shape to encase the catheter.

5. The catheter cover of claim 4 wherein the shape is cylindrical.

6. The catheter cover of claim 4 wherein the shape is rectangular.

7. The catheter cover of claim 1 wherein the single piece of the material of the elongated tubular body and the flange is fabricated from a material that is waterproof, pliable, and reusable.

8. The catheter cover of claim 7 wherein the material is composed of a plastic polymer compound that exhibits rubber-like characteristics.

9. The catheter cover of claim 7 wherein the material is composed of silicone rubber.

10. The catheter cover of claim 7 wherein the material is at least one of transparent, translucent, semi-translucent, opaque, or colored.

11. The catheter cover of claim 7 wherein the material is sanitized using alcohol and other suitable sanitizing methods.

12. The catheter cover of claim 1 wherein fabrication of the elongated tubular body and the flange as the single piece of the material is achieved through a process of injection molding.

13. The catheter cover of claim 1 wherein a moisture detection agent is inserted in the elongated tubular body.

14. The catheter cover of claim 13 wherein the moisture detection agent comprises litmus paper.

15. The catheter cover of claim 13 wherein the moisture detection agent is a permanganate crystal.

16. A waterproof catheter sheath comprising:
an elongated tubular body comprising an opening at a proximal end through which a catheter implanted in an upper chest area that hangs from an insertion site at a downward angle is inserted, wherein the elongated tubular body is closed at a distal end, wherein the elongated tubular body has closed sides from the distal end that is closed along a length of the elongated tubular body up to the opening at the proximal end to form a single cavity designed to encase the catheter, the length being greater in dimension than a width of the elongated tubular body; and
a flange integrated with the elongated tubular body at the proximal end to surround the opening, wherein the flange has a flat surface in a first plane to rest against a first portion of skin of the upper chest around an insertion perimeter of the insertion site, wherein an adhesive film is disposed over a rear surface of the flange in a second plane to create a seal against a second portion of the skin that surrounds the first portion of the skin, wherein the seal is created at an outer perimeter of the flange that is a located at a specified distance away from the insertion site, the insertion site comprising a center of the opening in the first plane, wherein a relative width of the flange is at least double, the relative width being between a first width between opposing sides of the outer perimeter of the flange in the first plan and a second width between opposing sides of an inner perimeter of the flange in the first plane, the inner perimeter being defined by the opening of the elongated tubular body, wherein the elongated tubular body is molded at an angle to accommodate the catheter that hangs from the insertion site at the downward angle, wherein the relative width being at least double increases a distance from the outer perimeter to the inner perimeter and increases an area of the rear surface of the flange such that a force required to break the seal between the flange and the skin is increased.

17. The waterproof catheter sheath of claim 16, wherein the elongated tubular body and flange are a molded silicone sheath.

18. The waterproof catheter sheath of claim 16, wherein the elongated tubular body is a molded silicone sheath to which the flange is secured.

19. The waterproof catheter sheath of claim 16, wherein the angle is between approximately 20 to 30 degrees.

20. The waterproof catheter sheath of claim 16, wherein the adhesive film is waterproof adhesive tape secured over the flange and at least a portion of the skin outside the outer perimeter of the flange.

\* \* \* \* \*